(12) United States Patent
Van et al.

(10) Patent No.: US 7,588,754 B2
(45) Date of Patent: Sep. 15, 2009

(54) BIODEGRADABLE POLYACETALS AND METHODS

(75) Inventors: Sang Van, San Diego, CA (US); Hyun Sik Chae, Oceanside, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 738 days.

(21) Appl. No.: 11/126,878

(22) Filed: May 10, 2005

(65) Prior Publication Data

US 2006/0257320 A1     Nov. 16, 2006

(51) Int. Cl.
*A61K 31/74*     (2006.01)
(52) U.S. Cl. .................. 424/78.27; 424/78.38
(58) Field of Classification Search ............... 424/78.27, 424/78.38
See application file for complete search history.

(56) References Cited

U.S. PATENT DOCUMENTS

| | | | |
|---|---|---|---|
| 4,745,161 | A | 5/1988 | Saudek et al. |
| 5,374,681 | A | 12/1994 | Kroner et al. |
| 5,811,510 | A | 9/1998 | Papisov |
| 5,863,990 | A | 1/1999 | Papisov |
| 5,958,398 | A | 9/1999 | Papisov |
| 6,878,374 | B2 | 4/2005 | Yu et al. |
| 2002/0031824 | A1 | 3/2002 | Greenberger |
| 2002/0082362 | A1 | 6/2002 | Brocchini et al. |
| 2002/0128177 | A1 | 9/2002 | Kirk et al. |
| 2003/0113303 | A1 | 6/2003 | Schwartz |
| 2003/0120355 | A1 | 6/2003 | Hafeli et al. |
| 2003/0186916 | A1 | 10/2003 | Yu et al. |
| 2003/0215395 | A1 | 11/2003 | Yu et al. |
| 2004/0166089 | A1 | 8/2004 | Yu et al. |
| 2004/0258669 | A1 | 12/2004 | Dzau et al. |
| 2005/0037401 | A1 | 2/2005 | Cammack et al. |
| 2005/0049387 | A1 | 3/2005 | Van et al. |
| 2005/0080033 | A1 | 4/2005 | Van et al. |
| 2005/0089503 | A1 | 4/2005 | Li et al. |
| 2006/0210530 | A1* | 9/2006 | Van et al. ................. 424/78.37 |

FOREIGN PATENT DOCUMENTS

| | | |
|---|---|---|
| EP | 0 683 177 | 11/1995 |
| WO | WO 9904824 | 2/1999 |
| WO | WO 2004009082 | 1/2004 |
| WO | WO2005/032597 | 4/2005 |
| WO | WO 2005/032597 | 4/2005 |

OTHER PUBLICATIONS

Hoppe (Die Makromolekular Chemie 124 (1969) 274-277).*
International Search Report for PCT/US2006/012420 filed on Apr. 3, 2006.
Written Opinion of the International Searching Authority for PCT/US2006/012420 filed on Apr. 3, 2006.

International Preliminary Report on Patentability dated Nov. 13, 2007 for PCT Application No. PCT/US2006/012420 filed Apr. 3, 2006.
Uhrich, K.E.; Cannizzaro, S.M.; Langer, R.S. and Shakeshelf, K.M. "Polymeric Systems for Controlling Drug Release." *Chem. Rev.* 1999, 99, 3181-3198.
Panyam J, Labhasetwar V. "Biodegradable nanoparticles for drug and gene delivery to cells and tissue." *Adv Drug Deliv Rev.* 2003, 55, 329-47.
Heller, J.; Barr, J.; Ng, S.Y.; Abdellauoi, K.S. and Gurny, R. "Poly(ortho esters): synthesis, characterization, properties and uses." *Adv. Drug Del. Rev.* 2002, 54, 1015-1039).
Kumar, N.; Langer, R.S. and Domb, A.J. "Polyanhydrides: an overview." *Adv. Drug Del. Rev.* 2002, 54, 889-91.
Bourke, S.L. and Kohn, J. "Polymers derived from the amino acid L-tyrosine: polycarbonates, polyarylates and copolymers with poly(ethylene glycol)." *Adv. Drug Del. Rev.*, 2003, 55, 447-466.
Tomlinson, R. et al., "Pendent Chain Functionalized Polyacetals That Display pH-Dependent Degradation: A Platform for the Development of Novel Polymer Therapeutics," Macromolecules 35, 473-480 (2002).
Tomlinson R, Heller J, Brocchini S, Duncan R. Polyacetal-doxorubicin conjugates designed for pH-dependent degradation. Bioconjug Chem. Nov.-Dec. 2003;14(6):1096-106.
Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers," J. Am. Chem. Soc. 124, 12398-12399 (2002).
International Search Report and Written Opinion dated Jul. 11, 2006 for International Application No. PCT/US2006/006568.
International Search Report and Written Opinion dated Aug. 18, 2006 for International Application No. PCT/US2006/012420.
International Preliminary Report on Patentability dated Sep. 18, 2007 for International Application No. PCT/US2006/006568.
Abbattista, et al. "Stem Cells and Kidney Diseases," *Minerva Medica*, vol. 95, No. 5, pp. 411-418, 2004.

(Continued)

*Primary Examiner*—Michael G. Hartley
*Assistant Examiner*—James W. Rogers
(74) *Attorney, Agent, or Firm*—Knobbe Martens Olson & Bear LLP

(57) ABSTRACT

Condensation polymerization methods are used to prepare various biodegradable polyacetals of the general formula (I). Such polymers are useful for variety of drug, biomolecule and imaging agent delivery applications.

9 Claims, 10 Drawing Sheets

OTHER PUBLICATIONS

Garcia-Castro, et al. "Antitumoral Cell-Based Therapies," *Cancer Therapy*, vol. 1, pp. 163-171, 2003.

Hardikar, "Generating New Pancreas from Old," *Trends in Endocrinology and Metabolism*, vol. 15, No. 5, pp. 198-203, Jul. 2004.

Hildebrandt, et al. "Optical Imaging of Transferrin Targeted PEI/DNA Complexes in Living Subjects," *Gene Therapy*, vol. 10, pp. 758-764, 2003.

Humes, et al. "Advances in Cell Therapy for Renal Failure" *Transplant Immunology*, vol. 12, pp. 219-227, 2004.

Kircheis, et al. "Tumor-Targeted Gene Delivery of Tumor Necrosis Factor-α Induces Tumor Necrosis and Tumor Regression Without Systemic Toxicity," *Cancer Gene Therapy*, vol. 9, pp. 673-680, 2002.

Melo, et al. "Molecular and Cell-Based Therapies for Protection, Rescue, and Repair of Ischemic Myocardium—Reasons for Cautious Optimism," *Circulation*, vol. 109, pp. 2386-2393, 2004.

U.S. Appl. No. 11/134,820, filed May 19, 2005.

U.S. Appl. No. 60/698,357, filed Jul. 11, 2005.

Ogris, et al. "Tumor-Targeted Gene Therapy: Strategies for the Preparation of Ligand-Polyethylene Glycol-Polyethylenimine/DNA Complexes," *Journal of Controlled Release*, vol. 91, pp. 173-181, 2003.

Russell, et al. "Immunohistochemical Characterisation of the Monoclonal Antibody BLCA-38 for the Detection of Prostate Cancer," *Cancer Immunol Immunother*, vol. 53, pp. 995-1004, 2004.

Sato, et al. "Monoclonal Antibody to HER-2/NEU Receptor Enhances Radiosensitivity of Esophageal Cancer Cell Lines Expressing HER-2/NEU Oncoprotein," *Int. J. Radiation Oncology Biol. Phys*, vol. 61, No. 1, pp. 203-211, 2005.

Saxon, et al. "Chemical and Biological Strategies for Engineering Cell Surface Glycosylation," *Annu. Rev. Cell Dev. Biol.*, vol. 17, pp. 1-23, 2001.

Smrekar, et al. "Tissue-Dependent Factors Affect Gene Delivery to Tumors in vivo," *Gene Therapy*, vol. 10, pp. 1079-1088, 2003.

* cited by examiner

BIODEGRADABLE POLYACETALS AND METHODS

BACKGROUND OF THE INVENTION

1. Field of the Invention

This invention relates generally to biodegradable polyacetals and methods for making them. These polymers are useful for a variety of drug, biomolecule and imaging agent delivery applications.

2. Description of the Related Art

A variety of systems have been used for the delivery of drugs, biomolecules, and imaging agents. For example, such systems include capsules, liposomes, microparticles, nanoparticles, and polymers. Polymers are often classified as being either biodegradable or nonbiodegradable.

A variety of polyester-based biodegradable systems have been characterized and studied. Polylactic acid (PLA), polyglycolic acid (PGA) and their copolymers polylactic-co-glycolic acid (PLGA) are some of the most well-characterized biomaterials with regard to design and performance for drug-delivery applications. See Uhrich, K. E.; Cannizzaro, S. M.; Langer, R. S. and Shakeshelf, K. M. "Polymeric Systems for Controlled Drug Release." Chem. Rev. 1999, 99, 3181-3198 and Panyam J, Labhasetwar V. "Biodegradable nanoparticles for drug and gene delivery to cells and tissue." Adv Drug Deliv Rev. 2003, 55, 329-47. Biodegradable systems based on polyorthoesters have also been investigated. See Heller, J.; Barr, J.; Ng, S. Y.; Abdellauoi, K. S. and Gurny, R. "Poly (ortho esters): synthesis, characterization, properties and uses." Adv. Drug Del. Rev. 2002, 54, 1015-1039. Polyanhydride systems have also been investigated. Such polyanhydrides are typically biocompatible and may degrade in vivo into relatively non-toxic compounds that are eliminated from the body as metabolites. See Kumar, N.; Langer, R. S. and Domb, A. J. "Polyanhydrides: an overview." Adv. Drug Del. Rev. 2002, 54, 889-91.

Amino acid-based polymers have also been considered as a potential source of new biomaterials. Poly-amino acids having good biocompatibility have been investigated to deliver low molecular-weight compounds. A relatively small number of polyglutamic acid and copolymers have been identified as candidate materials for drug delivery. See Bourke, S. L. and Kohn, J. "Polymers derived from the amino acid L-tyrosine: polycarbonates, polyarylates and copolymers with poly(ethylene glycol)." Adv. Drug Del. Rev., 2003, 55, 447-466.

Acid-sensitive polymers containing acetal linkages have been reported, see Tomlinson, R. et al., "Pendent Chain Functionalized Polyacetals That Display pH-Dependent Degradation: A Platform for the Development of Novel Polymer Therapeutics," Macromolecules 35, 473-480 (2002); Tomlinson R, Heller J, Brocchini S, Duncan R. Polyacetal-doxorubicin conjugates designed for pH-dependent degradation. Bioconjug Chem. 2003 November-December; 14(6):1096-106; and Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers," J. Am. Chem. Soc. 124, 12398-12399 (2002).

SUMMARY OF THE INVENTION

An embodiment provides a polymer comprising a recurring unit of the formula (I):

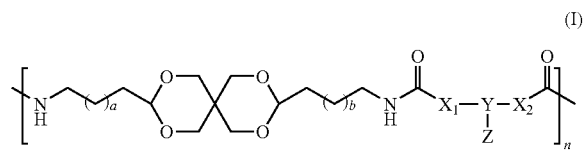

wherein:

$X_1$ and $X_2$ are each independently selected from the group consisting of single bond, —O—, —NR$^1$—, and —(CH$_2$)$_c$—CR$^1$R$^2$—;

Y is selected from the group consisting of N, $C_1$ to $C_{20}$ alkyl and $C_6$-$C_{20}$ aryl;

Z is selected from the group consisting of —(CH$_2$)$_m$—C(=O)OR$^3$, —(CH$_2$)$_m$—C(=O)SR$^3$, —(CH$_2$)$_m$—C(=O)NR$^3$R$^4$, —(CH$_2$)$_m$—NR$^3$R$^4$, —(CH$_2$)$_m$—NH—C(=O)—R$^3$, —NH—C(=O)—(CH$_2$)$_m$—C(=O)—NR$^3$R$^4$, —NH—C(=O)—(CH$_2$)$_m$—C(=O)—OA, —(CH$_2$)$_m$—NHR$^5$, —NH—C(=O)—(CH$_2$)$_m$—W, and —NH—C(=O)—(CH$_2$)$_m$-Het;

$R^1$, $R^2$ and $R^5$ are each independently selected from the group consisting of hydrogen, $C_1$ to $C_{20}$ alkyl, and $C_6$-$C_{20}$ aryl;

$R^3$ and $R^4$ are each independently selected from the group consisting of W, hydrogen, $C_1$ to $C_{20}$ alkyl, and $C_6$-$C_{20}$ aryl;

Het represents a heterocyclic ring;

W is selected from the group consisting of lactose, galactose, mannose, transferrin, antibody, antibody fragment, peptide, and imaging agent;

A is selected from the group consisting of succinimyl, H, and alkali metal;

a, b, c, and m are each independently zero or an integer in the range of 1 to 3; and n is an integer in the range of about 3 to about 10,000.

Another embodiment provides a method for making a polymer comprising a recurring unit of the formula (I), the method comprising reacting a compound of the formula (XII) with a compound of the formula (XIII):

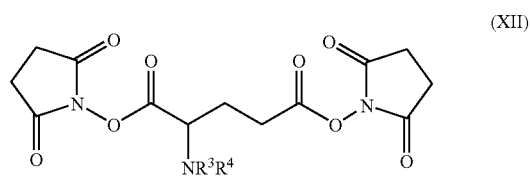

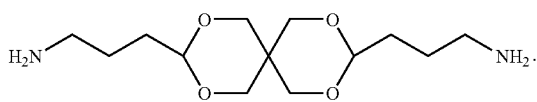

Another embodiment provides a method for making a polymer comprising a recurring unit of the formula (I), the method comprising reacting a compound of the formula (X) with a compound of the formula (XI):

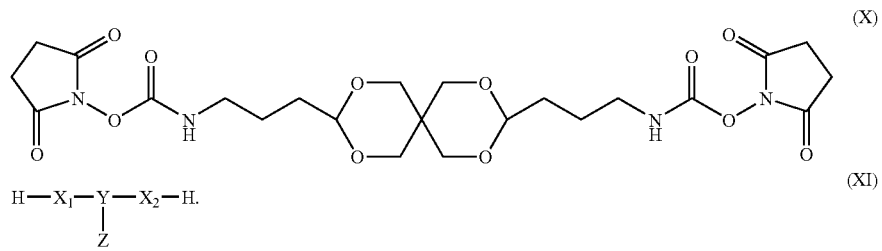

(X)

(XI)

Another embodiment provides a compound of the formula (X):

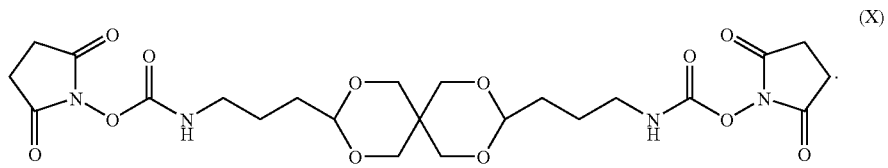

(X)

Another embodiment provides a method for making a compound of the formula (X) comprising reacting N,N'disuccinimidyl carbonate with 3,9-bis(3-aminopropyl)-2,4,8,10-tetraoxaspiro [5,5]undecane.

These and other embodiments are described in greater detail below.

DETAILED DESCRIPTION OF THE PREFERRED EMBODIMENTS

An embodiment provides a polymer comprising a recurring unit of the formula (I):

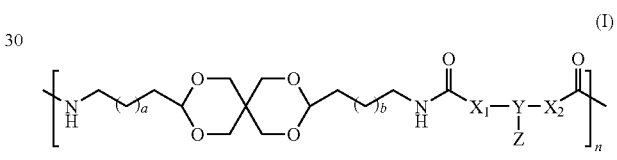

(I)

wherein:

$X_1$ and $X_2$ are each independently selected from the group consisting of single bond, —O—, —$NR^1$—, and —$(CH_2)_c$—$CR^1R^2$—;

Y is selected from the group consisting of N, $C_1$ to $C_{20}$ alkyl and $C_6$-$C_{20}$ aryl;

Z is selected from the group consisting of —$(CH_2)_m$—C(=O)$OR^3$, —$(CH_2)_m$—C(=O)$SR^3$, —$(CH_2)_m$—C(=O)$NR^3R^4$, —$(CH_2)_m$—$NR^3R^4$, —$(CH_2)_m$—NH—C(=O)—$R^3$, —NH—C(=O)—$(CH_2)_m$—C(=O)—$NR^3R^4$, —NH—C(=O)—$(CH_2)_m$—C(=O)—OA, —$(CH_2)_m$—$NHR^5$, —NH—C(=O)—$(CH_2)_m$—W, and —NH—C(=O)—$(CH_2)_m$-Het;

$R^1$, $R^2$ and $R^5$ are each independently selected from the group consisting of hydrogen, $C_1$ to $C_{20}$ alkyl, and $C_6$-$C_{20}$ aryl;

$R^3$ and $R^4$ are each independently selected from the group consisting of W, hydrogen, $C_1$ to $C_{20}$ alkyl, and $C_6$-$C_{20}$ aryl;

Het represents a heterocyclic ring;

W is selected from the group consisting of lactose, galactose, mannose, transferrin, antibody, antibody fragment, peptide, and imaging agent;

A is selected from the group consisting of succinimyl, H, and alkali metal;

a, b, c, and m are each independently zero or an integer in the range of 1 to 3; and n is an integer in the range of about 3 to about 10,000.

The symbols $X_1$, $X_2$, Y, Z, $R^1$-$R^5$, W, A, a, b, c, m, and n, as used elsewhere herein, have the same meaning as specified above, unless otherwise stated. Examples of polymers comprising a recurring unit of the formula (I) include polymers comprising one or more recurring units of the formulas (II) to (IX):

Polymers comprising a recurring unit of the formula (I) may be homopolymers or copolymers comprising two or more different recurring units of the formula (I), e.g., at least

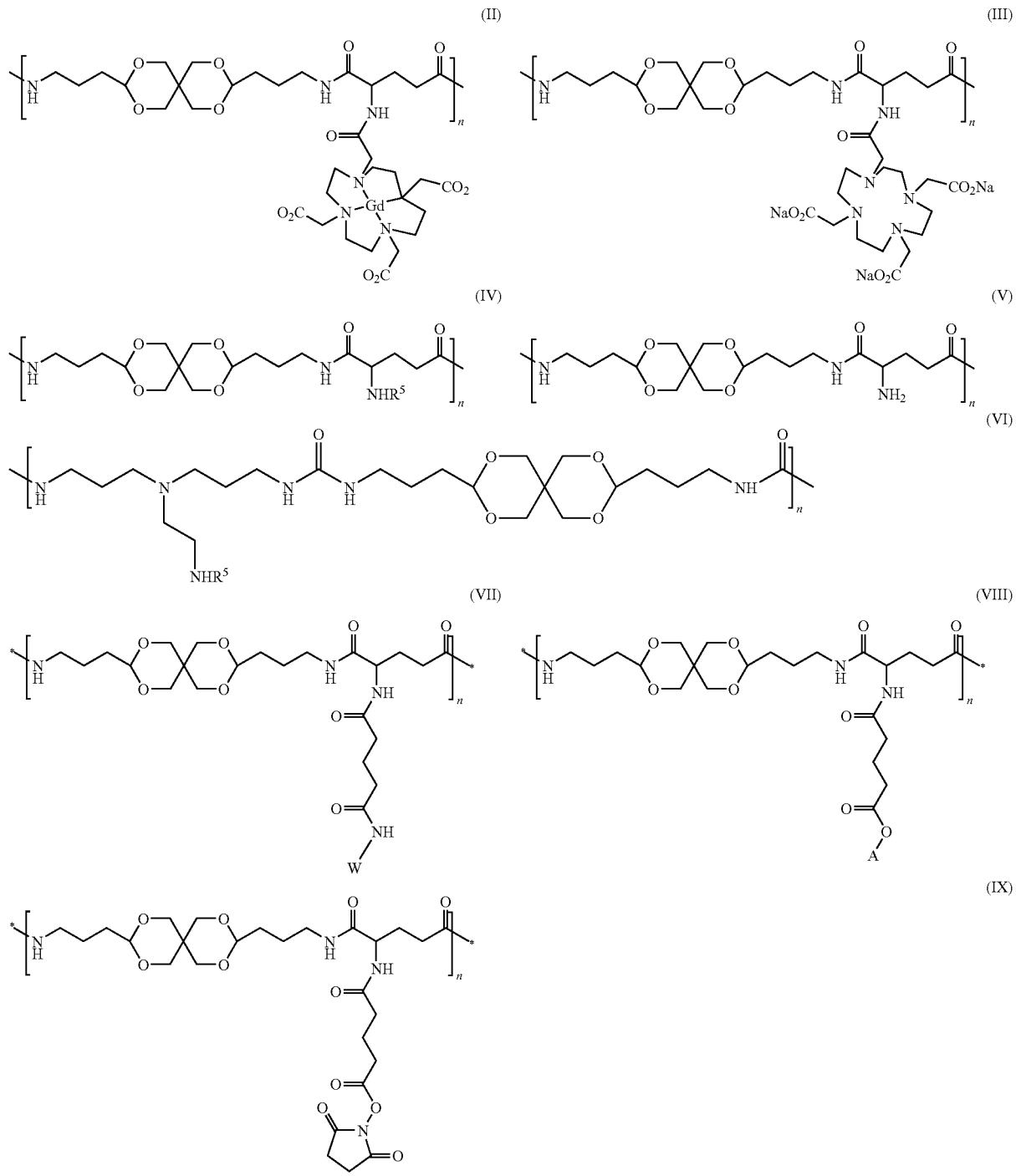

The recurring unit of the formula (II) is an example of a recurring unit of the formula (I) in which Z is —NH—C(=O)—$(CH_2)_m$—W and W is an imaging agent. The recurring unit of the formula (III) is an example of a recurring unit of the formula (I) in which Z is —NH—C(=O)—$(CH_2)_m$-Het.

two recurring units of the formulas (I) to (IX). For example, polymers comprising a recurring unit of the formula (I) may comprise at least two recurring units selected from the group consisting of a recurring unit of the formula (VII), a recurring unit of the formula (VIII), and a recurring unit of the formula (IX), wherein each n is individually in the range of about 3 to about 5,000. Polymers comprising a recurring unit of the formula (I) may be copolymers that comprise other recurring units that are not of the formula (I).

Figure 1:
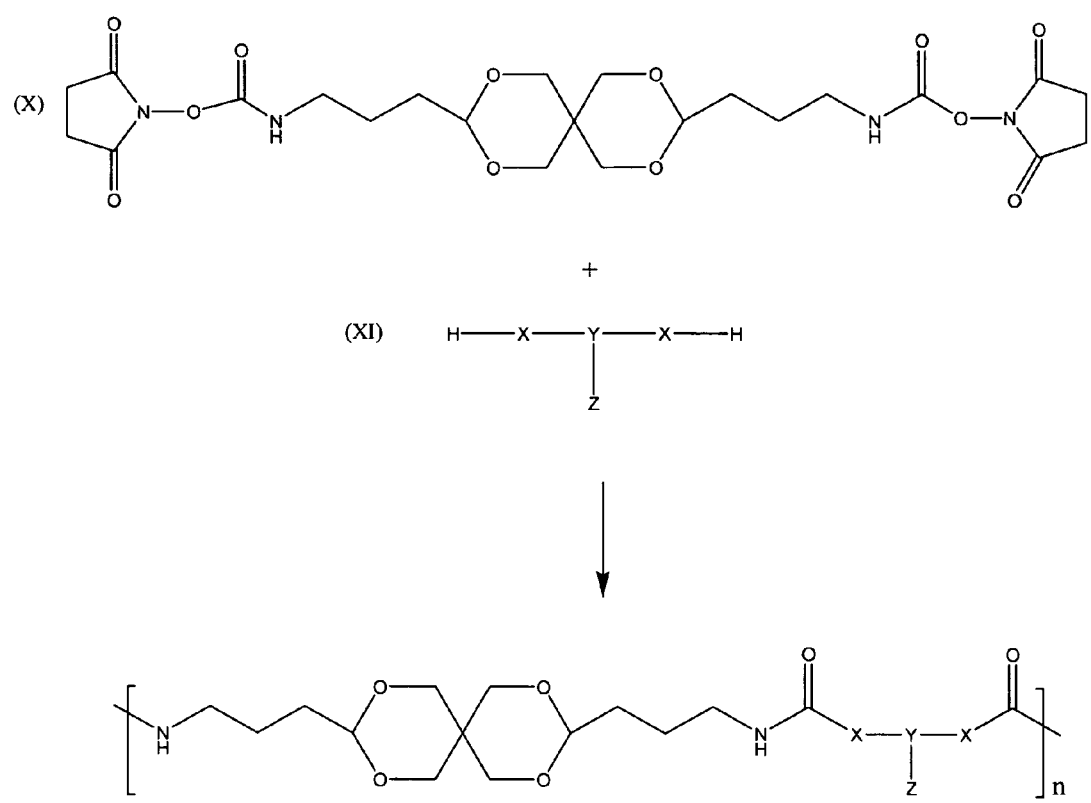
FIG. 1 is a reaction scheme illustrating an embodiment of a method for making a polymer comprising a recurring unit of the formula (I) that comprises reacting a compound of the formula (X) with a compound of the formula (XI).

Polymers comprising a recurring unit of the formula (I) may be prepared in various ways. For example, FIG. 1 illustrates a method for making a polymer comprising a recurring unit of the formula (I) that comprises reacting a compound of the formula (X) with a compound of the formula (XI):

The compound of the formula (X) is an example of a compound of the formula (XIV). Compounds of the formula (XIV) are useful for making polymers of the formula (I) and may be prepared in the general manner described in the Examples below for the preparation of the compound of the formula (X).

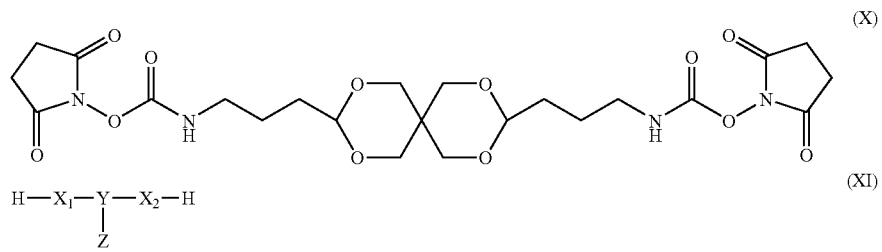

Figure 2:
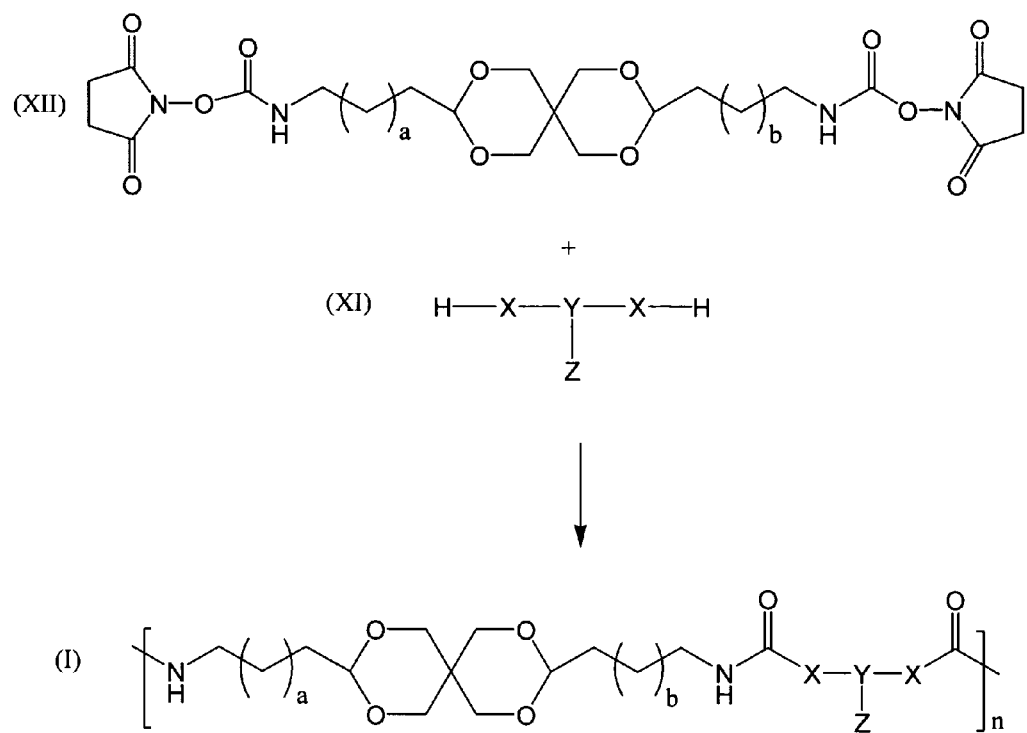
FIG. 2 is a reaction scheme illustrating an embodiment of a general method for making polymers that comprise a recurring unit of the formula (I).
Figure 6:
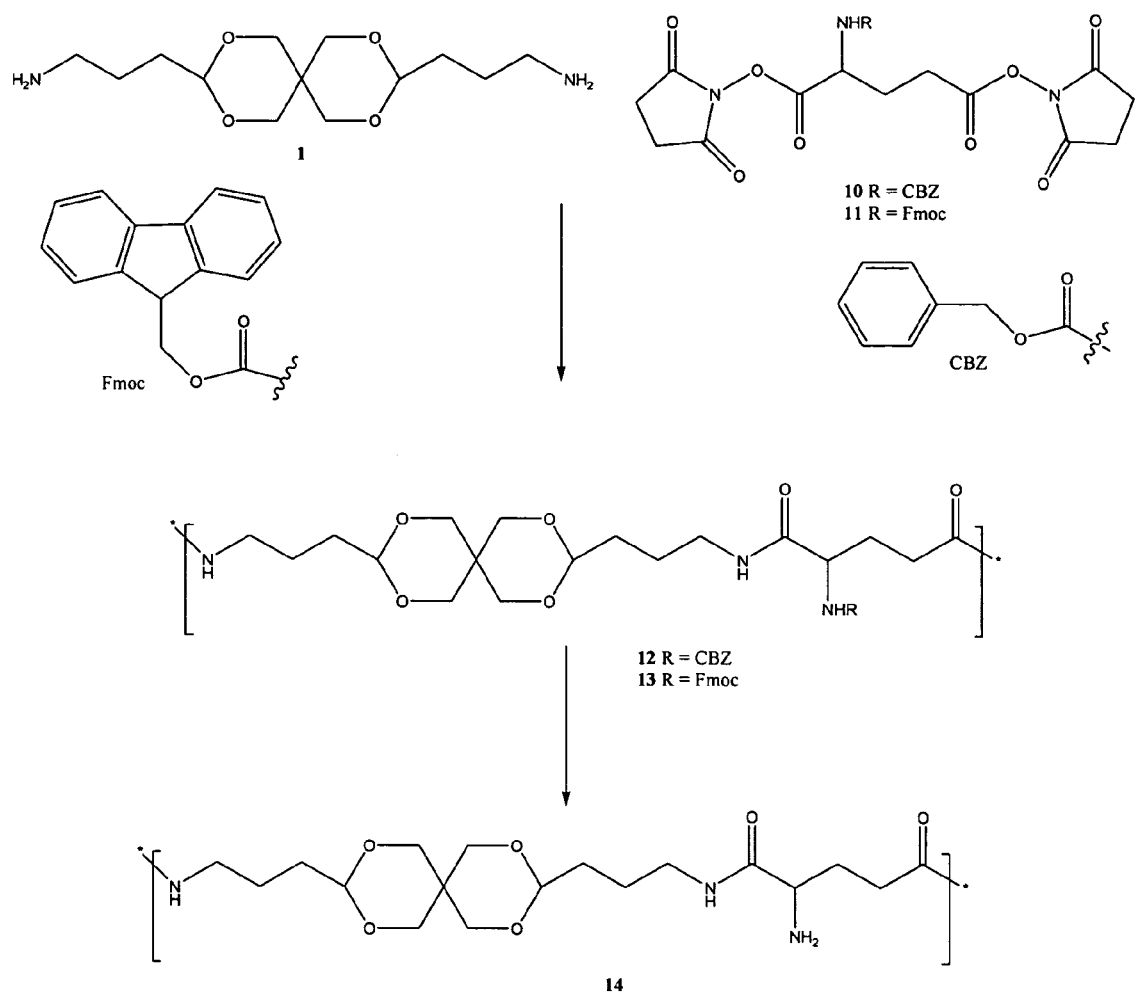
FIG. 6 is a reaction scheme illustrating an embodiment of a method of preparing a polymer of the formula (I).

A general reaction scheme for making polymers that comprise a recurring unit of the formula (I) is shown in FIG. 2. Reaction conditions suitable for carrying out the polymerizations illustrated in FIGS. 1, 2, and 6 are described in the Examples below. Those skilled in the art will understand that the reaction conditions may be varied to produce a wide variety of polymers comprising a recurring unit of the formula (I), including various homopolymers and copolymers. Polymers that comprise a recurring unit of the formula (I) may also be prepared by reacting a compound of the formula (XII) with a compound of the formula (XIII) under reaction conditions similar to those illustrated in FIGS. 1, 2, and 6 and described in the Examples below:

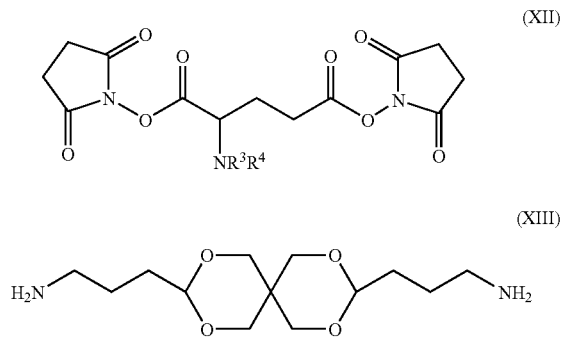

An embodiment provides a compound of the formula (XIV):

EXAMPLES

Solvents and reagents were purchased from commercial sources and used without further purification. All amounts and reaction times described below are approximate unless otherwise stated. Molecular weights (MW) are weight average and were determined by aqueous gel permeation chromatography (GPC) using polyethylene glycol standards. $^1$H and $^{13}$C data were measured at room temperature on a 400 MHz (100 MHz for $^{13}$C) in CDCl$_3$, D$_2$O or DMSO-d$_6$.

Example 1

Figure 3:
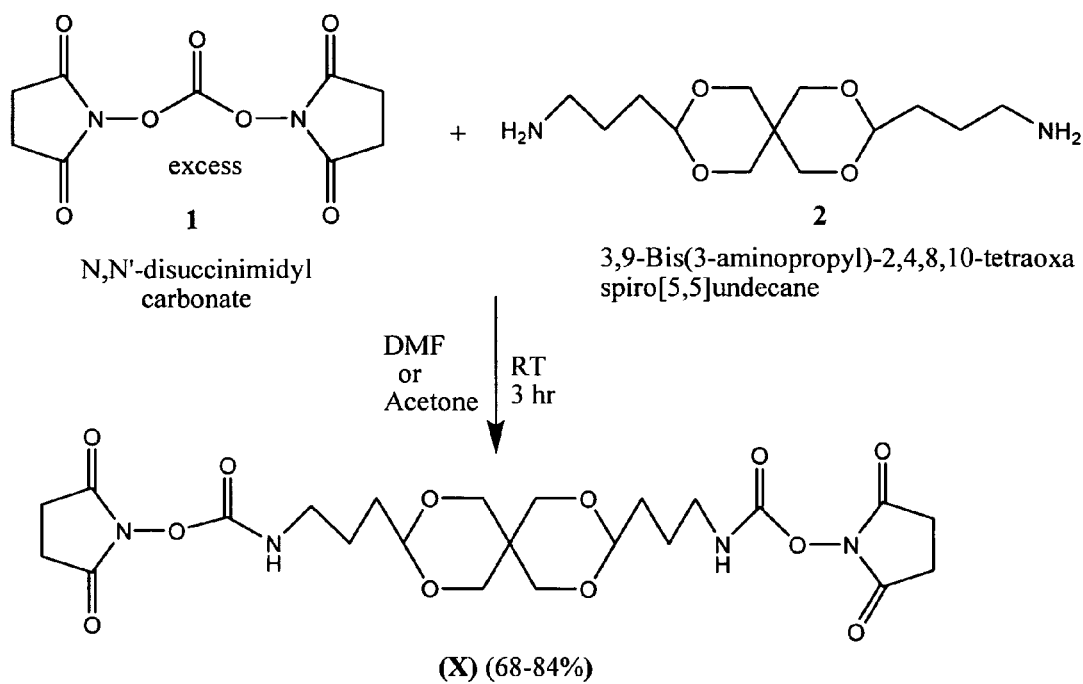
FIG. 3 is a reaction scheme illustrating an embodiment of a method for making a compound of the formula (X).

A compound of the formula (X) was prepared according to the general scheme illustrated in FIG. 3 as follows: To a stirred solution of 1 (5.17 g, 20 mmol) in DMF (40 mL), a solution of 2 (1.11 g, 4.0 mmol) in DMF (40 mL) was added dropwise under argon. The resulting mixture was stirred for 3 h at room temperature. The completeness of reaction was confirmed by TLC (100% ethyl acetate, R$_f$=0.38, stained with Molybate/cerium ammonium solution in H$_2$SO$_4$).

The DMF mixture was concentrated down by rotary evaporation. Water was added, and the product compound of the formula (X) was extracted with dichloromethane from water. The organic phase was dried over Na$_2$SO$_4$. Dichloromethane was removed by rotary evaporation and compound (X) was obtained (1.90 g, 84%) as a sticky pale yellow gel.

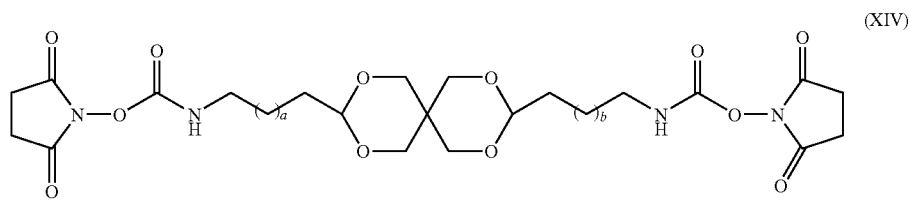

$^1$H NMR (CDCl$_3$, 400 MHz): 5.88, 4.47, 3.54, 3.24, 3.08, 2.78, 1.67. $^{13}$C NMR (CDCl$_3$): δ 170.1, 151.4, 102.1, 70.6, 70.1, 41.9, 32.3, 31.7, 25.6, 23.5.

Example 2

Additional compound (X) was prepared as described in Example 1, except that acetone was used in place of DMF and the yield was 68%.

Example 3

Figure 4:
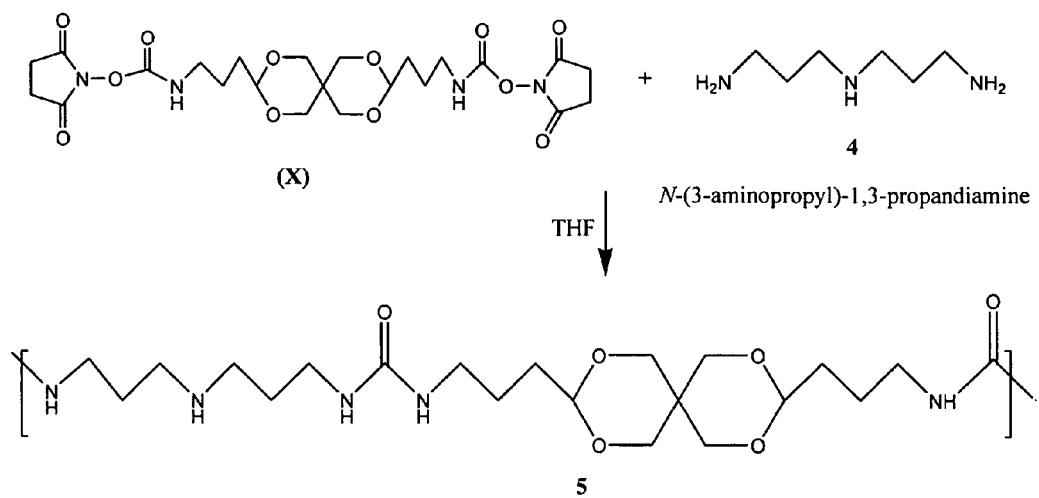
FIG. 4 is a reaction scheme illustrating an embodiment of a method of preparing a polymer of the formula (I) using a compound of the formula (X).

A polymerization was conducted using a compound of the formula (X) to prepare a polymer of the formula (I) according to the scheme illustrated in FIG. 4 as follows: To a stirred dichloromethane (DCM) solution (30 mL) of the compound (X) (0.34 g, 0.61 mmol), was added 4 (80 mg, 0.61 mmol, Aldrich Chemical Co.) in DCM (30 mL) under argon. Immediately, a white solid precipitated from the DCM mixture. The resulting mixture was stirred at room temperature under argon. The white precipitate was filtered out by a gravity filtration and the impure crude white solid (0.41 g) was dried in vacuum. The 0.41 g of crude white solid was redissolved in DMSO and excess acetone was added to induce precipitation and the solution mixture was stirred overnight. The residue was filtered and placed under high vacuum to yield 0.17 g of pale yellow oil as the product 5.
$^{13}$C NMR (DMSO): δ 158.8, 102.1. Observation of characteristic urea carbonyl peak at 158.8 ppm in $^{13}$C NMR and acetal peak at 102.1 ppm.

Examples 4-5

Figure 5:
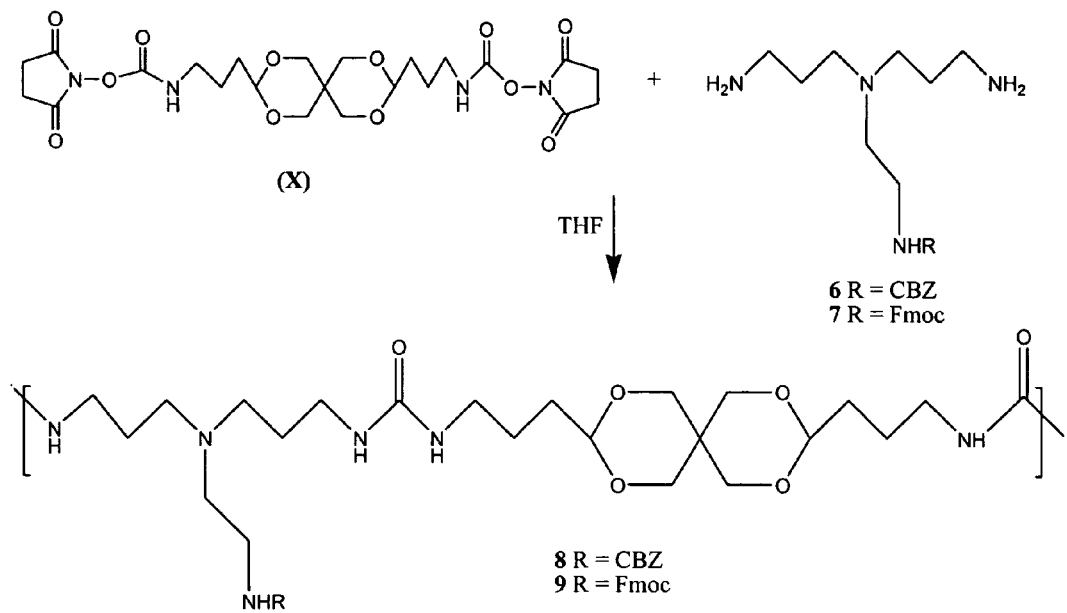
FIG. 5 is a reaction scheme illustrating an embodiment of a method of preparing a polymer of the formula (I).

Additional polymerizations were conducted in a manner similar to Example 3 to prepare polymers 8 and 9 of the formula (I) according to the scheme illustrated in FIG. 5.

Examples 6-10

Polymers 12, 13, and 14 of the formula (I) were prepared according to the scheme illustrated in FIG. 6 as follows: A solution of 10 (1.5 g, 3.2 mmol) in acetone (25 mL) was added into a solution of 1 (0.87 g, 3.2 mmol) in acetone (10 mL). White precipitate formed after a few minutes. The reaction mixture was stirred for 15 minutes. The solution was decanted and the residue was washed with more acetone, then dried under vacuum to provide 12 (0.87 g, 1.67 mmol). The MW of 12 is 45,417 daltons with PDI of 1.48. Similar reactions were carried out in DCM and DMF and produced additional amounts of 12 having molecular weights of 45,645 daltons (PDI 1.42) and 58,066 daltons (PDI 1.37), respectively. A similar reaction was carried in acetone to produce 13 having a MW of about 10,000-12,000 daltons.

The CBZ protecting group of 12 was removed by hydrogenation with catalytic 10% palladium/carbon under 1 atm hydrogen gas. Caution was taken because Pd/C is highly flammable when flammable solvents are near, including conducting the reaction under an inert atmosphere. 12 (4.0 g) was added into a 500-mL flask equipped with a stirring bar. Pd/C (10%, 0.5 g) was added into the flask. The flask was purged with argon. Deoxygenated methanol (150 mL) was added into the flask. Hydrogen gas (1 atm) was introduced and the mixture was stirred under 1 atm hydrogen gas for 1 day. The insoluble residue was filtered. The filtrate was concentrated by rotary evaporation and dried under vacuum to produce 14 (3.0 g). 14 may also be obtained from 13 by using 20% piperidine in DMF.

Example 11

Figure 7:
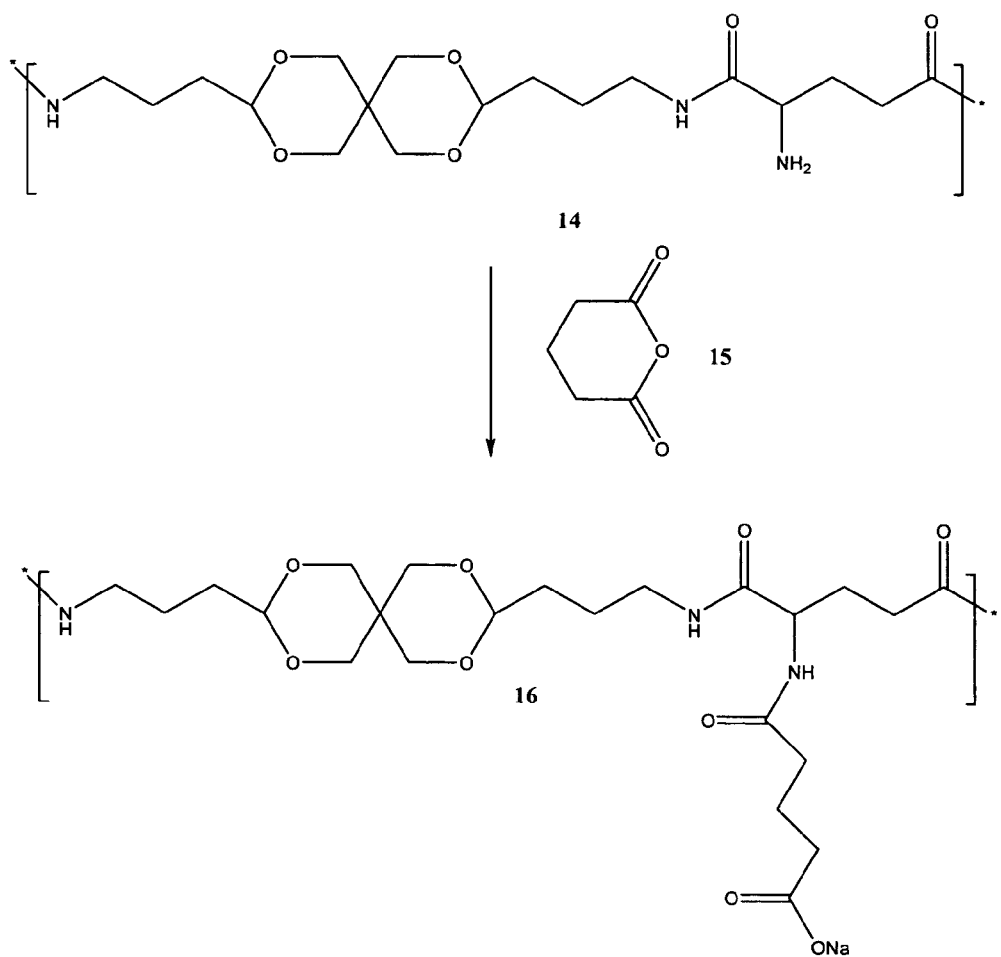
FIG. 7 is a reaction scheme illustrating an embodiment of a method of preparing a polymer of the formula (I).

Polymer 16 of the formula (I) was prepared according to the scheme illustrated in FIG. 7 as follows: 14 (2.7 g) was dissolved in dimethylacetamide (20 mL). Glutaric anhydride (15, 1.70 g) was added into the mixture and stirred for 1 day. The reaction was quenched with saturated sodium bicarbonate. Acetone was added to induce precipitation. The residue was filtered and redissolved in water. The product was dialyzed overnight using a cellulosic semi-permeable membrane (molecular weight cutoff=3,500 daltons). The product 16 (0.75 g) was obtained after the water was removed by rotary evaporation.

Example 12

Figure 8:
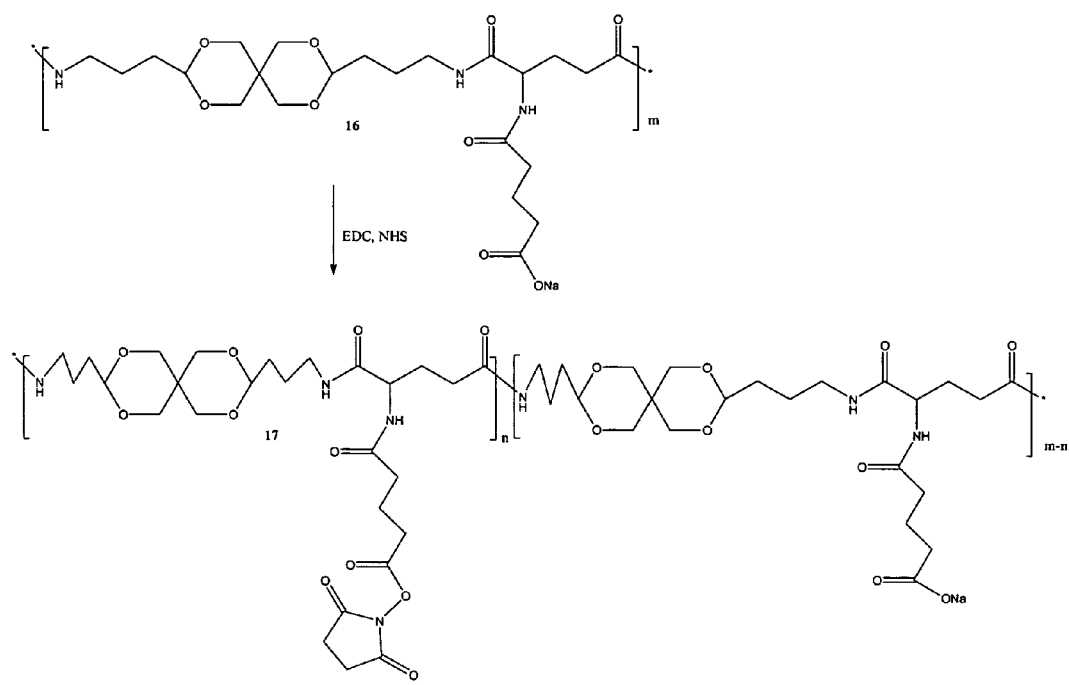
FIG. 8 is a reaction scheme illustrating an embodiment of a method of preparing a polymer of the formula (I).

Polymer 17 of the formula (I) was prepared according to the scheme illustrated in FIG. 8 as follows: 16 (1.0 g) was dissolved in water (10 mL). EDC (0.18 g) was added, and NHS (0.11 g) was added. The reaction was stirred for 30 min. The resulting solution was placed on a Sephadex-G25 chromatography column with water as eluent. The product 17 was obtained from the column fractions after freeze-drying.

Example 13-15

Figure 9:
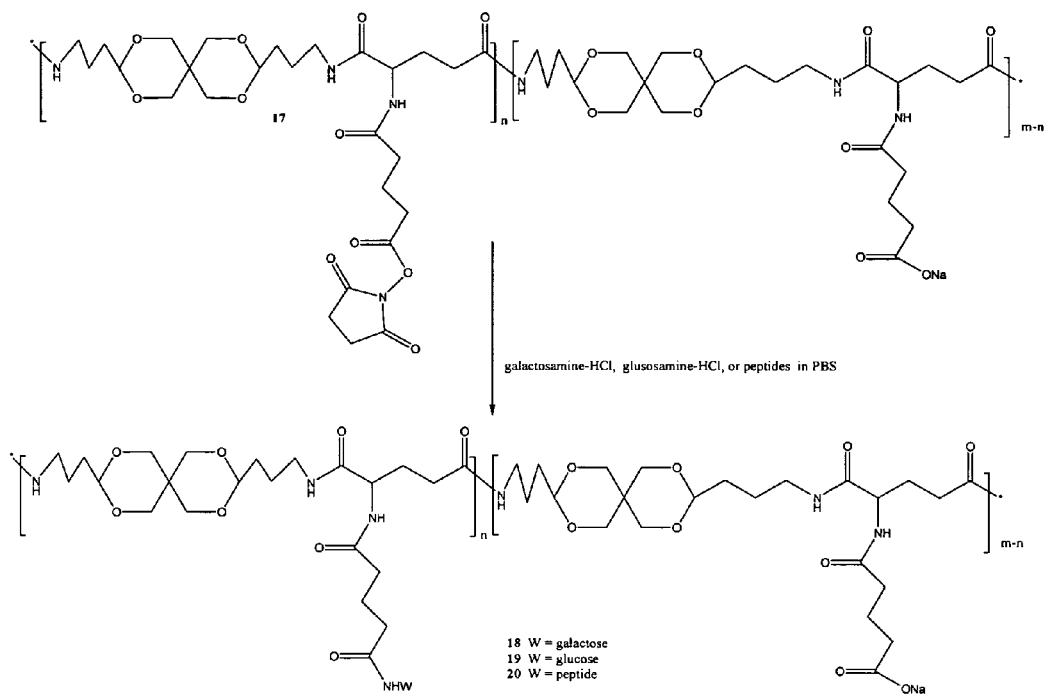
FIG. 9 is a reaction scheme illustrating an embodiment of a method of preparing a polymer of the formula (I).

Polymers 18-20 of the formula (I) were prepared according to the scheme illustrated in FIG. 9 as follows: Polyacetal 17 (50 mg) was dissolved in PBS (3 mL). Galactosamine-HCl (50 mg) was added into the mixture and stirred for 30 min. The solution was placed on the Sephadex-G25 chromatography column with water as eluent. The product 18 was obtained after freeze-drying the column fractions. Polymers 19 and 20 were obtained similarly.

Examples 16-17

Figure 10:
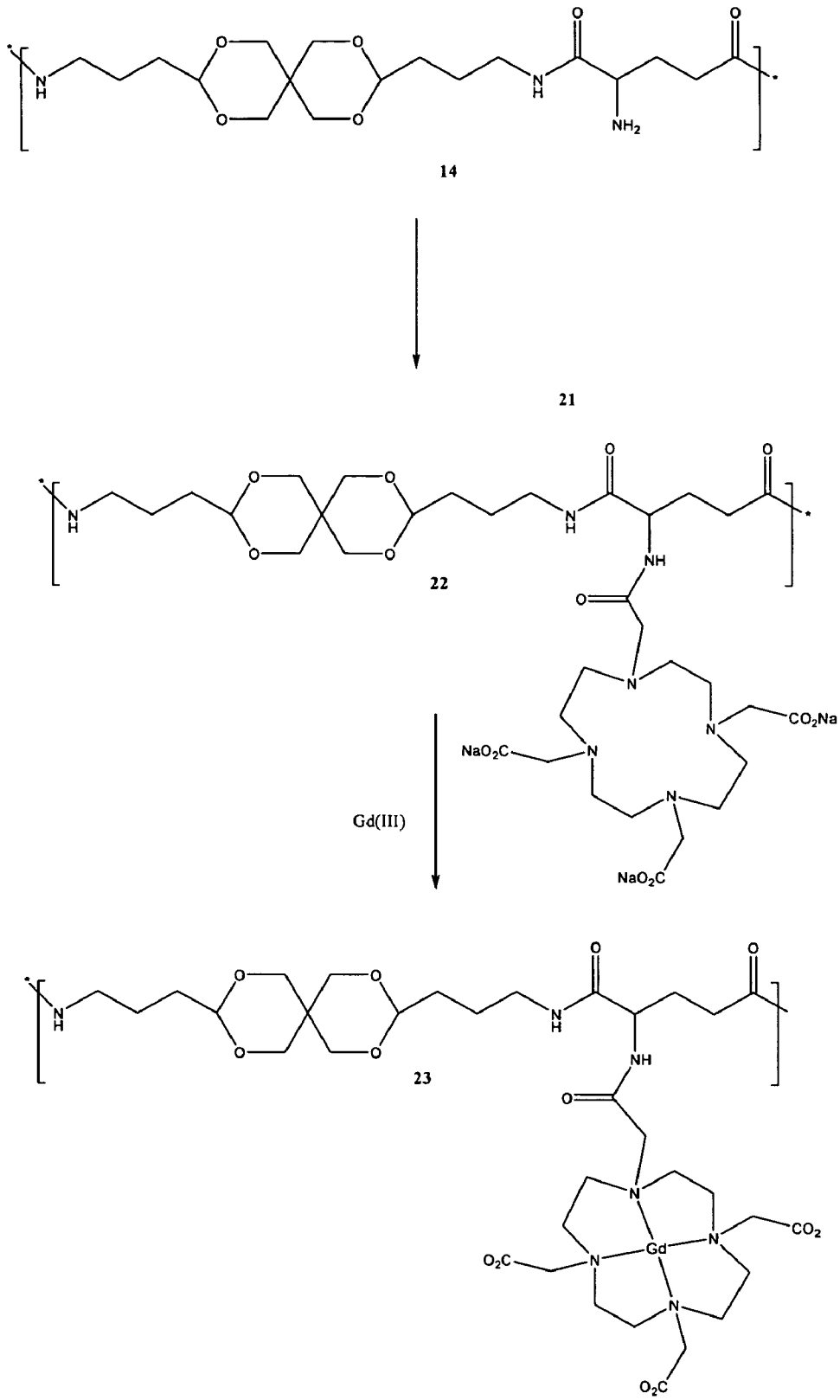
FIG. 10 is a reaction scheme illustrating an embodiment of a method of preparing a polymer of the formula (I).

Polymer 22 and 23 of the formula (I) were prepared according to the scheme illustrated in FIG. 10 as follows: Polymer 14 (30 mg) was dissolved in PBS (2 mL). Triethylamine (1 mL) was added in to the polymer solution. A solution of DOTA-NHS ester (100 mg, Macrocyclics, Inc) in PBS (1 mL) was added into the mixture. The mixture was stirred for 15 minutes. Water was removed by rotary evaporation. The crude residue was redissolved with distilled water (2 mL). Polymer 22 was purified by sephadex-G25 gel filtration. Polymer 22 (15 mg) was obtained after freeze-dried.

Polymer 22 (15 mg) was dissolved in PBS (1 mL). A solution of Gd(III)-Cl$_3$ (1 eq) in water (1 mL) was added and stirred for 15 minutes. Polymer 23 was purified by sephadex-G25 gel filtration. Polymer 23 (10 mg) was obtained after freeze-dried.

What is claimed is:

1. A polymer comprising a recurring unit of the formula (I):

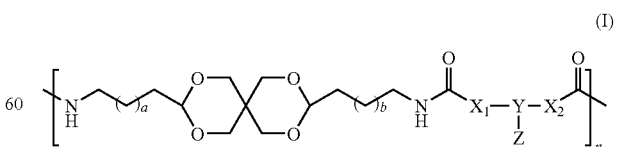

wherein:

$X_1$ and $X_2$ are each independently selected from the group consisting of single bond, —O—, —NR$^1$—, and —(CH$_2$)$_c$—CR$^1$R$^2$—;

Y is selected from the group consisting of N, $C_1$ to $C_{20}$ alkyl and $C_6$-$C_{20}$ aryl;

Z is selected from the group consisting of —$(CH_2)_m$—C(=O)O$R^3$, —$(CH_2)_m$—C(=O)S$R^3$, —$(CH_2)_m$—C(=O)N$R^3R^4$, —$(CH_2)_m$—N$R^3R^4$, —$(CH_2)_m$—NH—C(=O)—$R^3$, —NH—C(=O)—$(CH_2)_m$—C(=O)—N$R^3R^4$, —NH—C(=O)—$(CH_2)_m$—C(=O)—OA, —$(CH_2)_m$—NH$R^5$, —NH—C(=O)—$(CH_2)_m$—W, and —NH—C(=O)—$(CH_2)_m$-Het;

$R^1$, $R^2$ and $R^5$ are each independently selected from the group consisting of hydrogen, $C_1$ to $C_{20}$ alkyl, and $C_6$-$C_{20}$ aryl;

$R^3$ and $R^4$ are each independently selected from the group consisting of W, hydrogen, $C_1$ to $C_{20}$ alkyl, and $C_6$-$C_{20}$ aryl;

Het represents a heterocyclic ring;

W is an imaging agent;

A is selected from the group consisting of succinimyl, H, and alkali metal;

a, b, c, and m are each independently zero or an integer in the range of 1 to 3; and n is an integer in the range of about 3 to about 10,000.

2. The polymer of claim 1 of the formula (II):

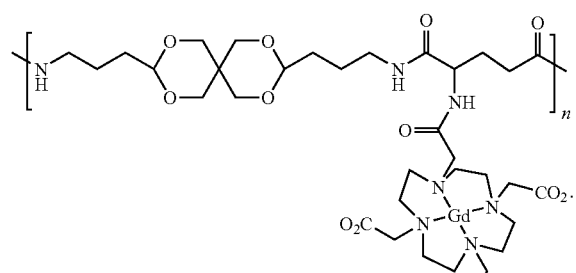

(II)

3. The polymer of claim 1 of the formula (III):

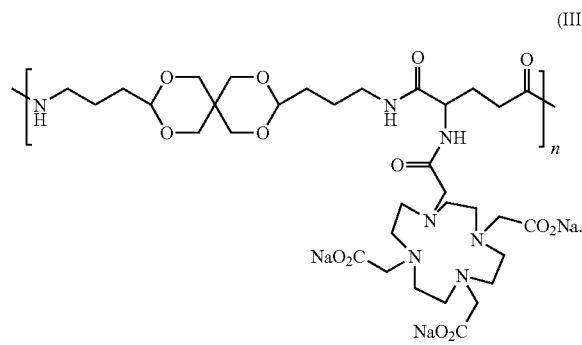

(III)

4. The polymer of claim 1 of the formula (IV):

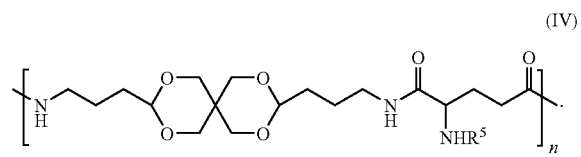

(IV)

5. The polymer of claim 1 of the formula (V):

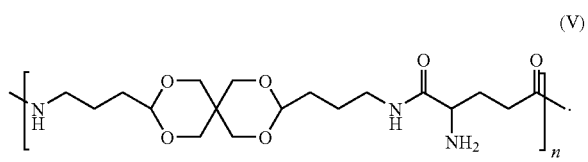

(V)

6. The polymer of claim 1 that is a copolymer comprising two or more different recurring units of the formula (I).

7. The polymer of claim 6 comprising at least two recurring units selected from the group consisting of a recurring unit of the formula (VII), a recurring unit of the formula (VIII), and a recurring unit of the formula (IX); wherein each n is individually in the range of about 3 to about 5,000:

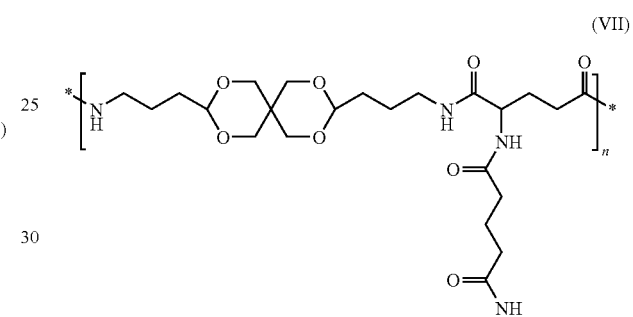

(VII)

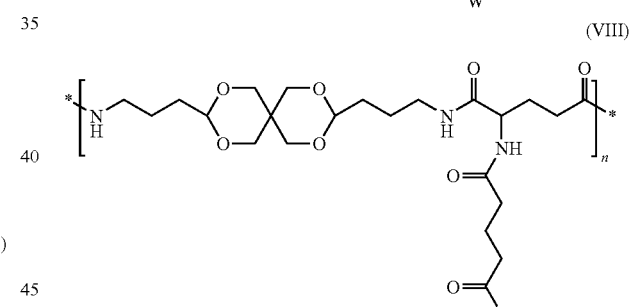

(VIII)

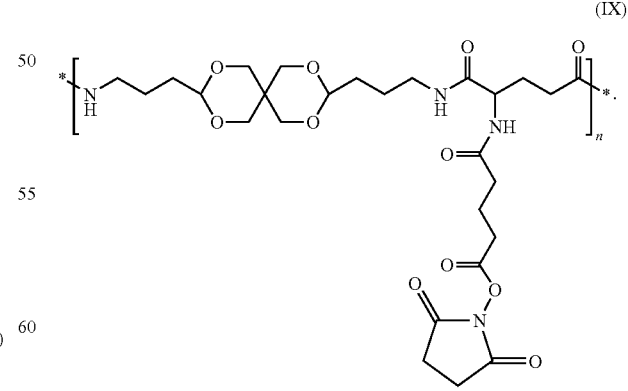

(IX)

8. A method of making the polymer of claim 1 comprising reacting a compound of the formula (X) with a compound of the formula (XI):

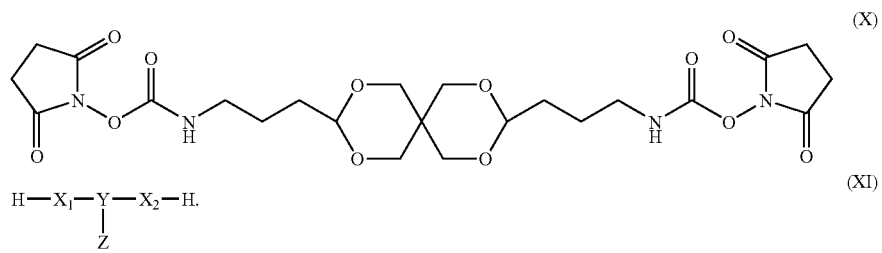
H—X$_1$—Y—X$_2$—H.
|
Z
9. A method of making the polymer of claim 1, comprising reacting a compound of the formula (XII) with a compound of the formula (XIII):
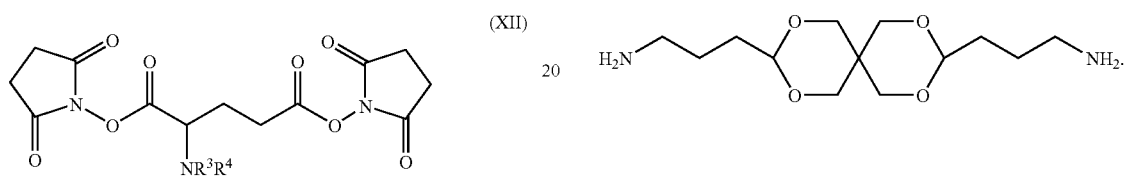
\* \* \* \* \*

UNITED STATES PATENT AND TRADEMARK OFFICE
CERTIFICATE OF CORRECTION

PATENT NO.        : 7,588,754 B2                                              Page 1 of 2
APPLICATION NO. : 11/126878
DATED             : September 15, 2009
INVENTOR(S)       : Van Sang, Hyun Sik and Lei Yu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1163 days.

Title Page, Item (56) At Page 1, Column 1, Line 5, under Foreign Patent Documents, below "WO WO2005/032597 4/2005" delete "WO WO2005/032597 4/2005".

Title Page, Item (56) At Page 1, Column 1, Line 1, under Other Publications, change "Makromolekular" to --Makromolekulare--.

Title Page, Item (56) At Page 1, Column 2, Line 5, under Other Publications, change "Controlling" to --Controlled--.

Title Page, Item (56) At Page 1, Column 2, Line 24, under Other Publications, change "Chem. Nov.-Dec. 2003" to --Chem. 2003 Nov.-Dec.--.

At Column 9, Line 55, change "with. catalytic" to --with catalytic--.

At Column 12, Line 16, in Claim 7, change "formula(VIII)," to --formula (VIII),--.

Signed and Sealed this

Twenty-first Day of September, 2010

David J. Kappos
*Director of the United States Patent and Trademark Office*

CERTIFICATE OF CORRECTION (continued)
U.S. Pat. No. 7,588,754 B2

At Column 13, Line 13, in Claim 8 change "$\underset{Z}{H-X_1-\overset{|}{Y}-X_2-H}$"

to -- $\underset{Z}{H-X_1-\overset{|}{Y}-X_2-H}$ wherein $X_1$, $X_2$, Y and Z are as defined within claim 1.--.